US007846921B2

(12) United States Patent
Rovati et al.

(10) Patent No.: US 7,846,921 B2
(45) Date of Patent: Dec. 7, 2010

(54) METHOD OF RELIEVING SYMPTOMS OF GASTROESOPHAGEAL REFLUX DISEASE

(75) Inventors: Lucio Claudio Rovati, Monza (IT);
Gianfranco Caselli, Milan (IT);
Massimo Maria D'Amato, Monza (IT);
Antonio Giordani, Pavia (IT);
Francesco Makovec, Lesmo (IT)

(73) Assignee: Rottapharm, S.p.A., Milan (IT)

( * ) Notice: Subject to any disclaimer, the term of this patent is extended or adjusted under 35 U.S.C. 154(b) by 158 days.

(21) Appl. No.: 11/575,264

(22) PCT Filed: Jul. 24, 2006

(86) PCT No.: PCT/EP2006/064567

§ 371 (c)(1),
(2), (4) Date: Mar. 14, 2007

(87) PCT Pub. No.: WO2007/014872

PCT Pub. Date: Feb. 8, 2007

(65) Prior Publication Data

US 2008/0004303 A1 Jan. 3, 2008

(30) Foreign Application Priority Data

Jul. 29, 2005 (EP) ................................. 05107042

(51) Int. Cl.
*A61K 31/547* (2006.01)
*A61K 31/454* (2006.01)
(52) U.S. Cl. .................................. 514/212.02; 514/339
(58) Field of Classification Search ....................... None
See application file for complete search history.

(56) References Cited

FOREIGN PATENT DOCUMENTS

WO          93/12817          7/1993

OTHER PUBLICATIONS

Hirschowitz, Bl, Yale J. Biol. Med., (Nov.-Dec. 1992), 65(6), 659-76.*
Tougas, Prevalence and Impact of Upper Gastrointestinal Symptoms in the Canadian Population: Findings From the Digest Study, The American Journal of Gastroenterology, vol. 94, No. 10, 1999.
Dent, Symptom evaluation in reflux disease: workshop background, processes, terminology, recommendations, and discussion outputs, Gut, 2004.
Lassen, Helicobacter pylori test-and-eradicate versus prompt endoscopy for management of dyspeptic patients: a randomised trial, The Lancet, vol. 356, Aug. 5, 2000.
Vakil, Review article: new pharmacological agents for the treatment of gastro-oesophageal reflux disease, Ailment Pharmacol Ther, vol. 19, pp. 1041-1049, 2004.
Crawley, How Satisfied Are Chronic Heartburn Sufferers with Their Prescription Medications? Results of the Patient Unmet Needs Survey, JCOM, vol. 7, No. 11, Nov. 2000.

Chiverton, Omeprazole (20 mg) daily given in the morning or evening; a comparison of effects on gastric acidity, and plasma gastrin and omeprazole concentration, Ailment. Pharmacol. Therap., vol. 6, pp. 103-111, 1992.
Hatlebakk, Nocturnal gastric acidity and acid breakthrough on different regimens of omeprazole 40 mg daily, Ailment Pharmacol Ther, vol. 12, pp. 1235-1240, 1998.
Katz, Gastric acidity and acid breakthrough with twice-daily omeprazole or lansoprazole, Ailment Pharmacol Ther, vol. 14, pp. 709-714, 2000.
Tytgat, Shortcomings of the first-generation proton pump inhibitors, European Journal of Gastroenterology & Hepatology, vol. 13 (suppl 1), pp. S29-S33, 2001.
Sachs, The Pharmacology of the Gastric Acid Pump: The H+,K+ ATPase1,2, Annu. Rev. Pharmacol. Toxicol., vol. 35, pp. 277-305, 1995.
Sachs, Improving on PPI-based therapy of GORD, European Journal of Gastroenterology & Hepatology, vol. 13 (suppl 1), 2001.
Sachs, Current trends in the treatment of upper gastrointestinal disease, Best Practice & Research Clinical Gastroenterology, vol. 16, No. 6, pp. 835-849, 2002.
Wurst, Current Status of Acid Pump Antagonists (Reversible PPIs), Yale Journal of Biology and Medicine, vol. 69, pp. 233-243, 1996.
Maton, Drug Therapy: Omeprazole, The New England Journal of Medicine, vol. 324, No. 14, pp. 993-1004, 1991.
Noble, International Union of Pharmacology. XXI. Structure, Distribution, and Functions of Cholecystokinin Receptors, Pharmacological Reviews, vol. 51, No. 4, pp. 745-781, 1999.
Crawley, Biological Actions of Cholecystokinin, Peptides, vol. 15, No. 4, pp. 731-755, 1994.
Woodruff, Cholecystokinin Antagonists, Annu. Rev. Pharmacol. Toxicol., vol. 31, pp. 469-501, 1991.
Schubert, Neural, Hormonal, and Paracrine Regulation of Gastrin and Acid Secretion, The Yale Journal of Biology and Medicine, vol. 65, pp. 553-560, 1992.
Rehfeld, The Tumor Biology of Gastrin and Cholecystokinin, Advances in Cancer Research, vol. 63, pp. 295-347, 1994.
Gonzalez, Pharmacological and molecular characterization of muscular cholecystokinin receptors in the human lower oesophageal sphincter, Neruogastroenterol. Mot., vol. 12, pp. 539-546, 2000.
Enochs, Changes in protein and nucleic acid synthesis in rat gastric mucosa after pentagastrin, Am. J. Physiol., vol. 223, No. 2, pp. E223-E228, 1977.
Modlin, The Gastric Enterochromaffin-like Cell: An Enigmatic Cellular Link, Gastroenterology, vol. 111, pp. 783-810, 1996.
McGowan, Helicobacter pylori and Gastric Acid: Biological and Therapeutic Implications, Gastroenterology, vol. 110, pp. 926-938, 1996.
Makovec, Characterization of antisecretory and antiulcer activity of CR 2945, a new potent and selective gastrin/CCKB receptor antagonist, European Journal of Pharmacology, vol. 369, pp. 81-90, 1999.

(Continued)

*Primary Examiner*—Phyllis G. Spivack
(74) *Attorney, Agent, or Firm*—Roylance, Abrams, Berdo & Goodman, L.L.P.

(57) ABSTRACT

The invention relates to a method for relieving or ameliorating symptoms of gastroesophageal reflux disease by administering a medicament that includes the cholecystokin-2 (CCK-2) receptor antagonist itriglumide and a proton pump inhibitor (PPI).

5 Claims, No Drawings

OTHER PUBLICATIONS

Omura, Establishment of Surgically Induced Chronic Acid Reflux Esophagitis in Rats, Scand. J. Gastroenterol., vol. 34, pp. 948-953, 1999.

Richter, Efficacy and Safety of Esomeprazole Compared With Omeprazole in GERD Patients With Erosive Esophagitis: A Randomized Controlled Trial, The American Journal of Gastroenterology, vol. 96, No. 3, pp. 656-665, 2001.

Parson, M, "Novel approaches to the pharmacological blockade of gastric acid secretion", Expert Opinion on Investigational Drugs, United Kingdom, vol. 14, No. 4, 2005, pp. 411-421.

* cited by examiner

METHOD OF RELIEVING SYMPTOMS OF GASTROESOPHAGEAL REFLUX DISEASE

FIELD OF THE INVENTION

The present invention relates to the combination of the cholecystokinin-2 (CCK-2) receptor antagonist Itriglumide and proton pump inhibitors (PPI) for the treatment of patients suffering from gastrointestinal or related disorders.

BACKGROUND OF THE INVENTION

Physicians have long recognised that conditions affecting the upper gastrointestinal (GI) tract commonly produce upper abdominal pain, discomfort, abdominal fullness, bloating, early satiety, nausea, vomiting, belching, heartburn and regurgitation. Such symptoms are typically postprandial and occur either alone or in combination. Overall, upper GI symptoms, including both dyspeptic-type and reflux-type, affect more than 25% of adults in the Western world and have a significant, negative impact on both functional status and sense of individual well-being (Tougas et al., Am J Gastroenterol. 1999; 94: 2845-2854). Symptoms related to disorders of upper gut function are among the most common presenting complaints in primary-care and GI specialty medical practice. These disorders commonly include, but are not limited to, GERD (gastroesophageal reflux disease), GERD with erosion, NERD (non-erosive reflux disease), NUD (non-ulcer dyspepsia), PUD (peptic ulcer disease), FD (functional dyspepsia), diabetic gastroparesis, gastrointestinal ulcers, Zollinger-Ellison syndrome, and antral G-cell hyperplasia.

Upper GI disorders are typically classified by anatomic region, e.g., those of esophageal origin and those of gastroduodenal origin, based on epidemiological evidence pointing to the existence of site-specific clusters of symptoms. However, the GI tract's anatomic continuity and integrated function in digestion and absorption of nutrients makes the separation of symptom clusters by site somewhat artificial. In fact, considering the diaphragm to be an anatomic boundary for defining upper GI disorders, e.g., attributing symptoms localised above the diaphragm such as heartburn to the esophagus, a thoracic organ, and symptoms localised below the diaphragm such as epigastric pain and discomfort to the stomach, an abdominal organ, has not been a very useful construct. For example, "heartburn" as the sole or predominant symptom to define gastroesophageal reflux disease (GERD) has very low sensitivity (38%) albeit high specificity (about 90%) (Dent et al., Gut. 2004, 53 (May): Supp 4:1-24). Rather than occurring alone as a manifestation of GERD, heartburn is associated with epigastric pain in at least two thirds of patients. Equally disturbing from the vantage point of defining upper GI disorders by location of symptoms, is the situation for dyspepsia. In a Danish study, 500 patients with dyspeptic symptoms (pain or discomfort in the epigastrium with or without heartburn, regurgitation, nausea, vomiting or bloating) were referred by their general practitioners for enrolment in a study comparing treatment strategies (*H. pylori* test—and eradicate versus prompt endoscopy) (Lassen et al, Lancet 2000, 356:455-460). Although the main entry criterion was epigastric pain or discomfort, which was reported by all patients, 32% had heartburn and/or regurgitation as their dominant symptom, which was almost as many patients as had dominant epigastric pain (37%). (See Lassen et al) Therefore, the available data indicate that significant overlap of symptoms exists in esophageal and gastric disorders; GERD patients have dyspeptic symptoms and dyspeptic patients have heartburn and/or regurgitation.

Given on the one hand the above described overlap of symptoms in patients with upper GI disorders and on the other hand the multiplicity of the underlying mechanisms of upper GI disorders, it is very unlikely that a pharmacological intervention directed versus a single chemical class represents an effective strategy for treating any upper GI disorders.

As the goal for the management of patients with upper GI disorders is aimed to provide symptom relief, improved quality of life and healing of any macroscopical lesion, if present, dyspeptic symptoms associated with upper GI disorders, therefore, represent an area of unmet need because there is no approved treatment for dyspeptic symptoms in patients. In addition, while there is compelling evidence for the effectiveness of acid suppression therapy in patients with symptomatic heartburn and/or regurgitation due to GERD, there is lack of convincing evidence of effectiveness of acid suppression therapy for dyspeptic symptoms associated with GERD. Indeed, it is a frequent observation that the majority of patients treated with a PPI for GERD symptoms are left with residual dyspeptic symptoms and treatment with standard PPI therapy for dyspeptic symptoms rarely show more than 10% efficacy advantage of PPI over placebo.

In addition, there are still some areas that can be identified where treatment of patients with GERD could be further refined or enhanced (Vakil N. Aliment Pharmacol Ther 2004; 19: 1041-1049), which include: lack of complete symptom control, as 75% of patients continued to experience heartburn frequently (Crawley J A, Schmitt C M. J Clin Outcomes Management 2000; 7: 29-34); variability in the inhibition of gastric acid secretion (Chiverton S G. Aliment Pharmacol Ther 1992; 6: 103-111); effective 24-h control of intragastric pH (Hatelbakk J G et al. Aliment Pharmacol Ther 1998; 12: 1235-1240; Katz P O et al. Aliment Pharmacol Ther 2000; 14: 709-714); onset of action, as all currently available PPS may take 3-5 days to achieve maximal acid inhibition at therapeutic doses (Tytgat G N. Eur J Gastroenterol Hepatol 2001; 13 (Suppl. 1): S29-33).

In particular, the slow onset of action is an intrinsic limitation of all exiting PPIs used a monotherapy in GERD as it is strictly linked to the pharmacokinetics and mode of action of all PPIs. After absorption and distribution PPIs given their $pK_a$ accumulate in the acid space of the canaliculus of secreting parietal cell where they are transformed into the active sulphenamide which forms non-competitive, covalent and irreversible bonds with the key cysteines of the $H^+$, $K^+$-APTase (Sachs G et al. Annu Rev Pharmacol Toxicol 1995; 35: 277-305). Due to the irreversible nature of this binding, a steady-state inhibition is achieved only after 3 or 4 days of treatment. This can be attributed to their very short half-life in combination with an activation of over 75% of the pumps and constant pump turnover in the face of covalent inhibition of the pump (Sachs G. Eur J Gastroenterol Hepatol. 2001; 13 (Suppl. 1): S35-S41).

Different strategies might be used to overcome the slow onset of action of all existing PPIs and possibly the scarce effect on dyspeptic symptoms.

For example new drugs are being developed such as the new class of Potassium-competitive acid blockers (P-CABs) which might offer a faster onset of action as these drugs bind ionically to the proton pump at or near the potassium-binding site in a $K^+$-competitive manner, thereby blocking acid secretion through a direct, reversible mechanism (Pope A J, Sachs G. Best Pract Res Clin Gastroenterol 2002; 16: 835-849; Wurts W, Hartmann M. Yale J Biol Med 1996; 69: 233-243).

An alternative approach might be represented by the combination of a PPIs to an anti-secretive drug acting with a different mechanism of action for example at receptors involved in the regulation of gastric acid secretion, like $H_2$ or CCK-2 (formerly "gastrin") receptor antagonist. These antagonists although not as efficacious as PPIs in inhibiting gastric acid secretion, act faster than PPIs as they are reversible antagonists, and therefore might be used in combination with PPIs to reach the goal of quickly achieving and then maintaining adequate inhibition of gastric acid secretion, thus with a faster and more complete symptom relief.

Of particular interest is the combination of PPIs with CCK-2 receptor antagonists which might offer a unique advantage among all anti-secretive drugs as, due to their mode of action, in addition to the antisecretive properties, they are also able to counteract the unavoidable consequences of the hypergastrinemia which inevitably accompanies the reduction of intragastric acid secretion, regardless of the means used to achieve it, as the reduced acidity inevitably leads to the increased release of gastrin by antral G cells (Maton P N. N Engl J Med 1991; 324: 965-975). In addition, CCK 2 receptor antagonists might be able to block other effects of cholecystokinin (CCK) and/or gastrin (see below).

CCK belongs to the group of substances known as brain-gut peptides and function as a neuropeptide and as a gut hormone. (Noble et al., Pharmacol. Rev. 1999, 51(4):745-781; Crawley et al., Peptides 1994, 15(4):731-755). It is now evident that at least two different receptors, namely CCK-1 (formerly CCKA or alimentary) and CCK-2 (formerly CCKB or brain) receptors, mediate CCK biological actions. (Noble et al., Pharmacol. Rev., 1999, 51(4):745-781; Woodruff and Hughes, Ann. Rev. Pharmacol. 1991, 31:469-501).

CCK is secreted primarily in response to meals and plays a well-recognised role in regulating gallbladder contraction and pancreatic enzyme secretion. Over the last decade, considerable evidence has emerged to support the concept that CCK plays an equally important role in the regulation of motor and sensory functions at various levels of the human upper GI tract. Specifically, the native peptide delays gastric emptying, modulates gastric sensory function (especially in response to fat), increases the rate of meal-induced, transient lower esophageal sphincter relaxations (TLESRs) and affects small bowel and colonic transit.

Gastrin is closely related to CCK and is secreted by G cells located in the gastric antral mucosa and upper small intestine. Gastrin exerts three main gastrointestinal effects: stimulation of acid secretion directly from parietal cells; stimulation of acid production via increased histamine release from enterochromaffin like (ECL) cells and stimulation of somatostatin release (Schubert et al., Yale J. Biol. Med 1992; 65: 553-60). Furthermore, gastrin has a trophic effect on the gastric mucosa and stimulates the growth of gastrin-sensitive malignant cells (Rehfeld et al., Adv. Cancer Res. 1994, 63: 295-347).

CCK/gastrin receptors have been classified based on their anatomical location. The $CCK_1$-subtype has been found in the gallbladder, pancreas and intestine. The $CCK_2$-subtype has been found in discrete regions of the brain such as the cerebral cortex, hippocampus, nucleus accumbens, caudate-putamen and thalamus. Extensive evidence now indicates that $CCK_1$ receptors are also present in the brain and conversely that $CCK_2$ receptors are also present in the periphery, principally in the stomach. Furthermore, both receptors are expressed on human lower esophageal sphincter (LOS) (Gonzales et al., Neurogastroenterol. Mot. 2000; 12, 539-546).

Gastrin is released in response to food or in response to the neutralisation of stomach pH (Walsh, Gastrointestinal Hormones in Physiology of the Gastrointestinal Tract. Johnos L. R. (Ed.), Raven Press: New York. 1987, 181-259). The increase of circulating gastrin plasma levels stimulates the proliferation of the oxyntic mucosal cells, in particular the parietal and ECL cells (Enochs et al., Am. J. Physiol. 1977, 223: E223).

Elevated fasted and postprandial gastrin levels have been described in several diseases such as peptic ulcer, Zoelliger-Ellison syndrome, gastrinomas, and G-cells hyperplasia (Modlin et al, Gastroenterology 1996, 111:783-810). Moreover chronic infection with *Helicobacter pylori* is associated with increased basal and gastrin stimulated gastric acid secretion (McGowan et al., Gastroenterology 1996, 110: 926-938).

Therefore, CCK2 receptor antagonists may have a therapeutic potentials as antisecretory drugs, in peptic ulcer disease as well as in all those pathological conditions characterised by an hypertrophy of the gastric mucosa.

Itriglumide (Code Number CR 2945), (R)-1-napthale-nepropanoic acid-β[2[(2-(8-azaspiro[4.5.]dec-8-ylcarbonyl) 4,6-dimethyl-phenyl]amino]-2-oxoethyl] is a novel, non peptide $CCK_2$ receptor antagonist developed by Rottapharm, formerly Rotta Research Laboratorium. The pharmacological profile of the compound is characterised by a high potency, selectivity and favourable toxicological profile (Makovec et al., Eur. J. Pharmacol., 1999, 369: 81-90).

Yet, the combination of a PPI and Itriglumide has not been described for a treatment of gastrointestinal disorders, even if some pharmaceutical compositions comprising CCK-B antagonists and a proton pump inhibitors to control gastric acid secretion in gastrointestinal disorders have been described in the literature. (See WO04/098610, WO04/101533, WO04/098609, WO03/041714, WO01/90078, WO01/85724, WO01/85723, WO01/85704, WO01/85167, and WO93/12817).

SUMMARY OF THE INVENTION

The subject matter of the invention is defined by the appended claims.

In one embodiment, the invention relates to treating gastrointestinal disorders by administering to a patient a first amount of Itriglumide and a second amount of a proton pump inhibitor (PPI). The subjects being treated are suffering from GERD (Gastroesophageal Reflux Disease), GERD with erosion, NERD (Non-Erosive Reflux Disease), NUD (Non-Ulcer Dyspepsia), PUD (Peptic Ulcer Disease), FD (Functional Dyspepsia), Diabetic Gastroparesis, Nocturnal heartburn, Heartburn, Bloating, gastrointestinal ulcers, Zollinger-Ellison syndrome and antral G-cell hyperplasia.

In another embodiment, the invention relates to a pharmaceutical composition for treatment of gastrointestinal disorders comprising (i) Itriglumide, (ii) a proton pump inhibitor (PPI) and (iii) a pharmaceutically acceptable carrier or excipient, wherein Itriglumide and PPI are present at therapeutically effective dosages to provide rapid and sustained relief effect.

DETAILED DESCRIPTION OF THE INVENTION

As specified above, the instant invention provides a novel drug combination of Itriglumide and a proton pump inhibitor for the treatment and prevention of gastrointestinal and other disorders. Preferably, the CCK-2 receptor antagonist Itriglumide and the proton pump inhibitor are administered at therapeutically effective dosages which, when combined, provide a rapid and sustained beneficial effect.

Definitions

Itriglumide can form salts and solvates which are also within the scope of this invention. Reference to Itriglumide is understood to include also its racemate mixture as well as salts and solvates thereof, unless otherwise indicated.

The term "combination" applied to active ingredients is used herein to define a single pharmaceutical composition (formulation) comprising both drugs of the invention (i.e., the CCK-2 receptor antagonist Itriglumide and a proton pump inhibitor) or two separate pharmaceutical compositions (formulations), each comprising a single drug of the invention (i.e., the CCK-2 receptor antagonist Itriglumide or a proton pump inhibitor), to be administered conjointly.

Within the meaning of the present invention, the term "conjoint administration" is used to refer to administration of the CCK-2 receptor antagonist Itriglumide and proton pump inhibitor simultaneously in one composition, or simultaneously in different compositions, or sequentially. For the sequential administration to be considered "conjoint", however, Itriglumide and proton pump inhibitor must be administered separated by a time interval that still permits to obtain rapid onset of action as well as good long-term efficacy for the treatment of gastrointestinal and related disorders. For example, the CCK-2 receptor antagonist and proton pump inhibitor must be administered on the same day (e.g., each—once or twice daily), preferably within an hour of each other, and most preferably simultaneously.

The term "treating" is used herein to mean to relieve, alleviate, delay or prevent at least one symptom of a disease in a subject. For example, in relation to a gastrointestinal disorder, the term "treat" may mean to relieve or alleviate at least one symptom selected from the group consisting of increased tension of the wall of a viscous, increased intravisceral pressure, cramps, colitis, gnawing, abdominal pain, constipation, diarrhoea, nausea, vomiting, urge to defecate, tenesmus, hematochezia, etc. Within the meaning of the present invention, the term "treat" also denote to arrest, delay the onset (i.e., the period prior to clinical manifestation of a disease) and/or reduce the risk of developing or worsening a disease.

For example, as disclosed herein, a prophylactic administration of Itriglumide in combination with a proton pump inhibitor can protect a recipient subject at risk of developing a gastrointestinal disorder. Similarly, according to the present invention, a therapeutic administration of Itriglumide conjointly with a proton pump inhibitor can lead to slow-down in the development of clinical symptoms or even regression of symptoms.

Within the meaning of the present invention, the term "proton pump inhibitor" is used to refer to compounds that can suppress the function of the hydrogen-potassium adenosine triphosphatase enzyme system to reduce the release of acid in the stomach and intestines. The most commonly known proton pump inhibitors include but are not limited to Omeprazole, Lansoprazole, Esomeprazole, Pantoprazole and Rabeprazole.

The CCK-2 receptor antagonist of the present invention is Itriglumide, Code Number CR 2945, namely (R)-1-napthalene-propanoic acid-β[2-[2-(8-azaspiro[4.5.]dec-8-ylcarbonyl)4,6-dimethylphenyl]amino]-2-oxoethyl]. This compound, its racemate and methods for their preparation are disclosed in WO98/00404 and WO97/02248, respectively.

Various salts and isomers (enantiomers) of Itriglumide can be used. The nature of the salt or isomer is not critical, provided that it is non-toxic and does not substantially interfere with the desired pharmacological activity.

The term "salts" includes salts of free bases.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, choline, diethanolamine, dicyclohexylamine, ethylenediamine and N-me-thylglucamine.

As used herein the term "therapeutically effective" applied to dose or amount refers to that quantity of a compound or pharmaceutical composition that is sufficient to result in a desired activity upon administration to a mammal in need thereof. More specifically, the term "therapeutically effective"refers to that quantity of a compound or pharmaceutical composition that is sufficient to reduce or eliminate at least one symptom of a gastrointestinal disorder.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable"means approved by a regulatory agency of the Federal or a state government or listed in the U.S. Pharmacopoeia or other generally recognised pharmacopoeia for use in mammals, and more particularly in humans.

The term "carrier" applied to pharmaceutical compositions of the invention refers to a diluent, excipient, or vehicle with which an active compound (e.g., an and/or) is administered. Such pharmaceutical carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil and the like. Suitable pharmaceutical excipients also include binding agents (e.g., pregelatinised maize starch, polyvinylpyrrolidone or hydroxypropyl methylcellulose); fillers (e.g., lactose, sucrose, glucose, mannitol, sorbitol and other reducing and non-reducing sugars, microcrystalline cellulose, calcium sulphate, or calcium hydrogen phosphate); lubricants (e.g., magnesium stearate, talc, or silica, steric acid, sodium stearyl fumarate, glyceryl behenate, calcium stearate, and the like); disintegrants (e.g., potato starch or sodium starch glycolate); or wetting agents (e.g., sodium lauryl sulphate), colouring and flavouring agents, gelatine, sweeteners, natural and synthetic gums (such as acacia, tragacanth or alginates), buffer salts, carboxymethylcellulose, polyethyleneglycol, waxes, inert carriers (e.g., ethanol, glycerol, water), suspending agents (e.g., sorbitol syrup, cellulose derivatives or hydrogenated edible fats), emulsifying agents (e.g., lecithin or acacia), non-aqueous vehicles (e.g., almond oil, oily esters, ethyl alcohol or fractionated vegetable oils), preservatives (e.g., methyl or propyl-p-hydroxybenzoates or sorbic acid), and the like. For other examples see "Remington's Pharmaceutical Sciences" by E. W. Martin, 18th Edition.

The term "subject" as used herein refers to a mammal (e.g., rodent such as mouse or rat). In particular, the term refers to humans.

The active agents of the present invention may be administered orally, topically, parenterally, or mucosally (e.g., buccally or rectally) in dosage unit formulations containing conventional non-toxic pharmaceutically acceptable carriers. It is usually desirable to use the oral route. The active agents may be administered orally in the form of a capsule or a tablet (see Remington's Pharmaceutical Sciences, Mack 5 Publishing Co., Easton, Pa.). The orally administered medicaments may be administered in the form of a modified release formulation or device, including diffusion-controlled systems, osmotic devices, dissolution-controlled matrices, and erodible/degradable matrices.

For oral administration in the form of a tablet or capsule, the active drug component can be combined with a non-toxic, pharmaceutically acceptable excipients such as binding agents, fillers, lubricants, disintegrants, colouring and flavouring agents, gelatine, sweeteners, natural and synthetic gums, buffer salts, carboxymethylcellulose, polyethyl-eneglycol and waxes.

Due to the fact that proton pump inhibitors are sensitive to pH environment, they need to be administered in a form protecting them from degradation in the stomach to allow them pass into the small intestine, the site of their absorption. On the contrary, Itriglumide does not need such protection.

For oral administration in liquid form, the drug components can be combined with non-toxic, pharmaceutically acceptable inert carriers, suspending agents, emulsifying agents, non-aqueous vehicles and preservatives. Stabilising agents such as antioxidants (e.g., BHA, BHT, propyl gallate, sodium ascorbate, and citric acid) can also be added to stabilise the dosage forms.

For liquid preparations the oral administration can take the form of, for example, solutions, syrups, emulsions or suspensions, or they can be presented as a dry product for reconstitution with water or other suitable vehicle before use. Preparations for oral administration can be suitably formulated to give controlled or postponed release of the active compound.

The active drugs can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines, as is well known.

Active drugs may also be coupled with soluble polymers as targetable drug carriers. Such polymers can include polyvinyl-pyrrolidone, pyran copolymer, polyhydroxy-propyl methacrylamide-phenol, polyhydroxy-ethyl-aspartamide-phenol, or polyethyleneoxide-polylysine substituted with palmitoyl residues.

Furthermore, active drug may be coupled to a class of biodegradable polymers useful in achieving controlled release of a drug, for example, polylactic acid, polyglycolic acid, copolymers of polylactic and polyglycolic acid, poly-epsilon caprolactone, polyhydroxybutyric acid, polyorthoesters, polyacetals, polyhydropyrans, polycyanoacrylates, and cross-linked or amphipathic block copolymers of hydrogels.

The formulations of the invention can be delivered parenterally, i.e., by intravenous (i.v.), subcutaneous (s.c.), intramuscular (i.m.), sub-dermal (s.d.), or intradermal (i.d.) administration, by direct injection, via, for example, bolus injection or continuous infusion. Formulations for injection can be presented in unit dosage form, e.g., in ampoules or in multi-dose containers, with an added preservative. The compositions can take such forms as excipients, suspensions, solutions, or emulsions in oily or aqueous vehicles, and can contain formulatory agents such as suspending, stabilising and/or dispersing agents. Alternatively, the active ingredient can be in powder form for reconstitution with a suitable vehicle, e.g., sterile pyrogen-free water, before use.

Compositions of the present invention can also be formulated for rectal administration, e.g., as suppositories or retention enemas (e.g., containing conventional suppository bases such as cocoa butter or other glycerides).

As disclosed herein, a proton pump inhibitor and the CCK-2 receptor antagonist Itriglumide can be mixed with excipients which are pharmaceutically acceptable and compatible with the active ingredients. In addition, if desired, the preparations may also include minor amounts of auxiliary substances such as wetting or emulsifying agents, pH buffering agents, and/or agents that enhance the effectiveness of the pharmaceutical composition.

Although the active agents of the present invention may be administered in divided doses, for example, two or three times daily, a single daily dose of each is preferred, with a single daily dose of both agents in one composition or in two separate compositions administered simultaneously being most preferred.

The instant invention also encompasses a process for preparing pharmaceutical compositions comprising combining the CCK-2 receptor antagonist Itriglumide and a proton pump inhibitor with a pharmaceutically acceptable carrier and/or excipient.

Preferred specific amounts of the proton pump inhibitor which may be used in unit dosage amounts of the invention include, for example, 10 to 40 mg for the PPI. Preferred specific amounts of Itriglumide which may be used in unit dosage amounts of the invention include, for example, 100 mg-600 mg.

The invention also provides a pharmaceutical pack or kit comprising one or more containers containing one or more of the ingredients of the formulations of the invention. In a related embodiment, the present invention provides a kit for the preparation of the pharmaceutical compositions of the invention, said kit comprising the CCK-2 receptor antagonist Itriglumide in a first container, and a proton pump inhibitor in a second container, and, optionally, instructions for admixing the two drugs and/or for administration of the compositions. Each container of the kit may also optionally include one or more physiologically acceptable carriers and/or excipients and/or auxiliary substances. Associated with such container(s) can be a notice in the form prescribed by a governmental agency regulating the manufacture, use or sale of pharmaceuticals or biological products, which notice reflects approval by the agency of manufacture, use or sale for human administration.

The compositions may, if desired, be presented in a pack or dispenser device which may contain one or more unit dosage forms containing the active ingredient. The pack may, for example, comprise metal or plastic foil, such as a blister pack. The pack or dispenser device may be accompanied by instructions for administration. Compositions of the invention formulated in a compatible pharmaceutical carrier may also be prepared, placed in an appropriate container, and labelled for treatment of an indicated condition.

The compositions of the invention may be administered in a modified release formulation. Modified release dosage forms provide a means for improving patient compliance and for ensuring effective and safe therapy by reducing the incidence of adverse drug reactions. Compared to immediate release dosage forms, modified release dosage forms can be used to prolong pharmacologic action after administration, and to reduce variability in the plasma concentration of a drug throughout the dosage interval, thereby eliminating or reducing sharp peaks.

The majority of modified release dosage forms comprise a core either coated with or containing a drug. The core is then coated with a release modifying polymer within which the drug is dispersed. The release modifying polymer disintegrates gradually, releasing the drug over time. Thus, the outermost layer of the composition effectively slows down and thereby regulates the diffusion of the drug across the coating layer when the composition is exposed to an aqueous environment, i.e. the gastrointestinal tract. The net rate of diffusion of the drug is mainly dependent on the ability of the gastric fluid to penetrate the coating layer or matrix and on the solubility of the drug itself.

According to the methods of the present invention, the pharmaceutical compositions described herein are administered to a patient at therapeutically effective doses, preferably, with minimal toxicity. Preferably, the proton pump inhibitor and the CCK-2 receptor antagonist Itriglumide are each used at a dosage which, when combined, provide an enhanced effect, most preferably, an effect not observed upon administration of each agent alone.

The efficacy of Itriglumide, PPI and their combination was determined in preclinical studies using small animal models (e.g., rats) in which both the Itriglumide and proton pump inhibitor have been found to be therapeutically effective and in which these drugs can be administered by the same route proposed for the human clinical trials.

For any pharmaceutical composition used according to the invention, the therapeutically effective dose can be estimated initially from animal models to achieve a circulating plasma concentration range that includes the IC50 (i.e., the concentration of the test compound which achieves a half-maximal inhibition). Dose-response curves derived from animal systems are then used to determine testing doses for the initial clinical studies in humans. In safety determinations for each composition, the dose and frequency of administration should meet or exceed those anticipated for use in the clinical trial.

As disclosed herein, the dose of the CCK-2 receptor antagonist Itriglumide in the compositions of the present invention is determined to ensure that the dose administered continuously or intermittently will not exceed an amount determined after consideration of the results in test animals and the individual conditions of a patient. A specific dose naturally varies (and is ultimately decided according to the judgment of the practitioner and each patient's circumstances) depending on the dosage procedure, the conditions of a patient or a subject animal such as age, body weight, sex, sensitivity, feed, dosage period, drugs used in combination, seriousness of the disease, etc. As disclosed herein, an appropriate dose of a Itriglumide is generally in the range of 2 to 10 mg per kg of the body weight/day.

Toxicity and therapeutic efficacy of the compositions of the invention can be determined by standard pharmaceutical procedures in experimental animals, e.g., by determining the LD50 (the dose lethal to 50% of the population) and the ED50 (the dose therapeutically effective in 50% of the population). The dose ratio between therapeutic and toxic effects is the therapeutic index and it can be expressed as the ratio ED50/LD50. Compositions that exhibit large therapeutic indices are preferred.

The data obtained from animal studies can be used in formulating a range of doses for use in humans. The doses of derivatives used in humans are preferably within a range of circulating concentrations that include the ED50 with little or no toxicity. The dosage can vary within this range depending upon the dosage form employed and the route of administration utilised.

The drug combination of the invention is not only highly effective at relatively low doses but also possesses low toxicity and produces few side effects.

Preclinical Studies

The combination treatment of Itriglumide with omeprazole, taken as the representative of PPIs, has been studied in comparison with the monotherapy of the same drugs in two models of acute and chronic esophagitis in rats, mimicking human reflux esophagitis conditions.

Effect on Acute Reflux Esophagitis in Rats

Male rats of 175-200 g body weight were fasted for 24 hours prior the experiment. Water was allowed ad libitum. Under ether anaesthesia, the abdomen was incised along the midline, and both pylorus and limiting ridge (transitional region between the forestomach and corpus) were simultaneously ligated. Consequently, the total capacity of the stomach to hold gastric juice was greatly diminished, resulting in reflux of gastric juice into the esophagus. Following ligation of pylorus and limiting ridge, the test compounds were given intraduodenally (5 ml/kg), and the abdomen was closed by suturing. After 3 hours, rats were killed by ether overdose and the gastroesophageal portion was excised. The lesion in the thoracic esophagus was scored macroscopically, using a lesion index according to the following criteria: no lesion as 0; oedema as 1; reddening as 2; the length of hemorrhagic area <20 mm as 3; the length of hemorrhagic area 20-30 mm as 4; the length of hemorrhagic area 30-40 mm as 5; the length of hemorrhagic area >40 mm or perforation as 6.

The doses of the tested compounds which reduce of 50% the esophagus lesions ($ED_{50}$) were calculated from the dose-response regression line.

The results thus obtained are given in Table 1.

TABLE 1

Protective effects of Itriglumide, omeprazole and their combination treatment on acute reflux esophagitis in pylorus-ligated rats

| Treatment Group | Doses (mg/kg) | Average Score lesions | % Effect vs. control | $ED_{50}$ |
|---|---|---|---|---|
| Control | Saline | 5.1 | — | — |
| Itriglumide | 2.5 | 5.2 | 0 | |
|  | 5.0 | 3.7 | 27.5 | 9.1 mg/kg |
|  | 10 | 2.5 | 51.0 | |
|  | 20 | 0.9 | 82.3 | |
| Control | Saline | 5.8 | — | — |
| Omeprazole | 0.1 | 5.6 | 3.4 | |
|  | 0.3 | 5.8 | 0 | 4.9 mg/kg |
|  | 1.0 | 4.8 | 17.2 | |
|  | 3.0 | 2.7 | 53.4 | |

TABLE 1-continued

Protective effects of Itriglumide, omeprazole and their combination treatment on acute reflux esophagitis in pylorus-ligated rats

| Treatment Group | Doses (mg/kg) | Average Score lesions | % Effect vs. control | $ED_{50}$ |
|---|---|---|---|---|
| Control | Saline | 5.6 | — | |
| Itriglumide + Omeprazole | 2.5 + 0.3 | 4.8 | 14.3 | (Itriglumde + 0.3 mg/kg |
| " | 2.5 + 1.0 | 4.0 | 28.6 | Omeprazole) = 5.3 mg/kg |
| " | 5.0 + 0.3 | 2.5 | 55.4 | |
| " | 5.0 + 1.0 | 1.4 | 75.0 | |
| " | 10 + 0.3 | 1.5 | 73.2 | (Itriglumide + 1.0 mg/kg |
| " | 10 + 1.0 | 0.3 | 94.6 | Omeprazole) = 3.6 mg/kg |

The calculated protective effects of Itriglumide and Omeprazole administered separately were 9.1 mg/kg and 4.9 mg/kg, respectively.

The combination treatment of two compounds produced an increase in the protective effect. The calculated ED50 for the combination treatment were 5.3 mg/kg for Itriglumide plus Omeprazole (0.3 mg/kg) and 3.6 mg/kg for Itriglumide plus Omeprazole (1 mg/kg), respectively.

In average the combination treatment produced a synergistic increasing efficacy for both examined drugs. For example, as disclosed herein, the combination treatment of 5 mg/kg Itriglumide plus 1 mg/kg Omeprazole produced an 75% protective effect versus a 45% expected, this latter being the sum of the results obtained with the equivalent separate drug treatment, i.e. 27.5 and 17.2% of protective effect, respectively.

Effect on Chronic Acid Reflux Esophagitis in Rat

The method was according to Omura N., et al. (Scand. J gastroenterol. 1999; 34:948-953) with slight modifications.

Male Wistar rats, 10 weeks old, were kept in controlled animal room 1 week prior to use and fed with standard diet. A day before the experiment rats were deprived of food but allowed free access to water.

Surgery

This model consists of gastric outlet obstruction obtained by ligation of forestomach and pyloric stenosis. Rats were operated under air/halothane anaesthesia; after opening the abdomen with a median incision, the transitional region between forestomach and the glandular portion was ligated and then the forestomach was blocked with other two ligations. Pyloric stenosis were obtained by wrapping a duodenum near the pylorus with a piece (about 2 mm) of a catheter (3.5 mm inner diameter) as a ring. The ring was closed by thermocautery and fixed to the pylorus with a nylon thread. The abdomen was closed by suturing.

After the operation the rats (10 animals per group) were deprived of diet for 48 h but had free access to water.

Drug Efficacy

Drugs were administered once a day, starting on day zero, by subcutaneous injection. During the experiment body weight as well as the mortality were recorded.

The animals were killed 15 days later by overdose of ether inhalation. The abdomen was opened and the esophagus excised and placed on a cork plate. The presence and extension of esophagitis sites was evaluated by macroscopic observation. Each site of esophagitis was measured (mm of length× mm of width). Data were expressed as $mm^2$ of esophagitis area (mean area group). The results are shown in Table 2.

TABLE 2

Protective effects of itriglumide, omeprazole and their combination treatment on a chronic model of reflux esophagitis in rats

| Treatment Group | Doses (mg/kg) | Survival Rate (%) | Occurrence of Esophagitis | Total average size of ulcers ($mm^2$) | % Protection vs. control | $ED_{50}$ (mg/kg) |
|---|---|---|---|---|---|---|
| Control | — | 80 | 8/8 | 57 | — | — |
| Itriglumide | 10 | 90 | 4/9 | 33 | 42.1 | — |
| Omeprazole | 0.5 | 80 | 6/8 | 47 | 17.5 | 2.2 |
| " | 1 | 90 | 6/9 | 41 | 28.0 | |
| " | 2 | 90 | 3/9 | 29 | 49.1 | |
| Itriglumide (10 mg/kg) + Omeprazole | 0.5 | 90 | 2/9 | 16 | 71.9 | 0.16 |
| Itriglumide (10 mg/kg) + Omeprazole | 1 | 100 | 1/10 | 6 | 89.5 | |
| Itriglumide (10 mg/kg) + Omeprazole | 2 | 100 | 0/10 | 0 | 100 | |

The combination treatment of Itriglumide with a PPI may offer many advantages.

Itriglumide has a rapid onset of action by blocking the gastrin receptor and reducing acid secretion. On the contrary, PPIs are metabolised in the gastric parietal cells to give the active sulphenimide metabolites that inactivate the sulphydryl group of the proton pump, thus blocking the hydrogen-ion secretion. This process requires some time and PPIs may take up to 3-5 days to achieve maximal efficacy in inhibiting gastric acid secretion and 5 to 8 days to induce a complete a sustained resolution of heartburn (Richter J E et al. 2001: 96: 656-665).

Therefore, by combining Itriglumide with PPIs, it is possible to obtain rapid onset of action, as well as good long-term efficacy. Furthermore, the gastric pH increasing effect produced by Itriglumide may increase the absorption of the acid-labile PPIs, allowing the drugs to reach the upper small intestinal region in an intact, absorbable unionised form. This speculation may explain the synergic effect exhibited by the combination treatment in both acute and chronic esophagitis experiments shown previously.

In fact, the results shown in Tables 1 and 2 demonstrate that the Omeprazole-Itriglumide combination treatment may allow to strongly reduce the Omeprazole dosage, maintaining at the same time the same efficacy. This effect and the concomitant blocking activity of Itriglumide on gastrin receptor may offer the possibility to reduce the risk, especially during long-term therapy, of hyperplasia of the ECL-cells in the gastric mucosa, induced by the increase in the serum gastrin due to a long-lasting achlorhydria situation. In addition if gastrin via activation of CCK-2 receptors is implicated in the pathogenesis of dyspeptic symptoms, the combination of Itriglumide and PPIs might offer the additional advantage of providing a complete symptom relief.

It should be understood that the invention is not limited to the particular embodiments described herein, but that various changes and modifications may be made without departing from the spirit and scope of this novel concept as defined by the following claims.

The invention claimed is:

1. A method for relieving or alleviating symptoms of gastroesophageal reflux disease by administering a medicament comprising: (i) a CCK-2/gastrin antagonist itriglumide, or its racemate or a pharmaceutically acceptable salt thereof and (ii) an ATP-ase proton pump inhibitor selected from the group consisting of omeprazole, esomeprazole, lansoprazole, pantoprazole, rabeprazole, and pharmaceutically acceptable salts thereof, in an amount sufficient to relieve or alleviate symptoms of gastroesophageal reflux disease.

2. A method according to claim 1, wherein said medicament comprises (i) itriglumide or its racemate, and (ii) a proton pump inhibitor in a form suitable for conjoint administration.

3. A method according to claim 1, wherein the proton pump inhibitor is omeprazole.

4. The method according to claim 1, wherein said amount sufficient results in an increased efficacy for treating said gastrointestinal disorders greater than the added efficacy of (i) or (ii).

5. A method for relieving or alleviating symptoms of gastroesophageal reflux disease by administering a synergistic combination of compounds which comprise: (i) a CCK-2/gastrin antagonist itriglumide, or its racemate or a pharmaceutically acceptable salt thereof and (ii) an ATP-ase proton pump inhibitor selected from the group consisting of omeprazole, esomeprazole, lansoprazole, pantoprazole, rabeprazole, and pharmaceutically acceptable salts thereof, in a synergistically therapeutic amount sufficient to relieve or alleviate symptoms of gastroesophageal reflux disease.

\* \* \* \* \*